United States Patent
Florissant et al.

(10) Patent No.: US 10,561,363 B1
(45) Date of Patent: Feb. 18, 2020

(54) MEDICATION ALERT WATCH

(71) Applicants: Islande Florissant, Amityville, NY (US); Edny Florissant, Amityville, NY (US)

(72) Inventors: Islande Florissant, Amityville, NY (US); Edny Florissant, Amityville, NY (US)

(*) Notice: Subject to any disclaimer, the term of this patent is extended or adjusted under 35 U.S.C. 154(b) by 373 days.

(21) Appl. No.: 15/334,338

(22) Filed: Oct. 26, 2016

(51) Int. Cl.
*A61B 5/02* (2006.01)
*A61B 5/00* (2006.01)
*A61B 5/022* (2006.01)
*A61B 5/024* (2006.01)
*G08B 5/36* (2006.01)

(52) U.S. Cl.
CPC .......... *A61B 5/681* (2013.01); *A61B 5/02233* (2013.01); *A61B 5/02438* (2013.01); *A61B 5/7275* (2013.01); *A61B 5/742* (2013.01); *G08B 5/36* (2013.01); *A61B 2560/0214* (2013.01)

(58) Field of Classification Search
CPC . A61B 5/681; A61B 5/02233; A61B 5/02438; A61B 5/7275; A61B 5/742; A61B 2560/0214; G08B 5/36
See application file for complete search history.

(56) References Cited

U.S. PATENT DOCUMENTS

| 5,050,142 | A | | 9/1991 | Gibbs | |
|---|---|---|---|---|---|
| 5,157,640 | A | | 10/1992 | Backner | |
| 5,485,848 | A | * | 1/1996 | Jackson | A61B 5/0002 600/485 |
| 6,075,755 | A | * | 6/2000 | Zarchan | A61J 7/0481 368/10 |
| 7,542,379 | B2 | | 6/2009 | Kimel | |
| 8,647,268 | B2 | | 2/2014 | Tran | |
| 8,787,120 | B2 | * | 7/2014 | Fleury | G04B 19/12 368/205 |
| 8,920,332 | B2 | * | 12/2014 | Hong | A61B 5/02427 600/500 |
| D729,652 | S | | 5/2015 | Nuovo | |
| 9,069,333 | B1 | | 6/2015 | Romans | |
| 2009/0040874 | A1 | | 2/2009 | Rooney | |

FOREIGN PATENT DOCUMENTS

WO 9938052 A1 7/1999

* cited by examiner

*Primary Examiner* — Eric J Messersmith

(57) ABSTRACT

The medication alert watch is a medical instrument that is adapted for use with a person. The medication alert watch is adapted to be worn on a wrist of the person. The medication alert watch comprises a control system, a cuff mechanism, a heart sensor, a power system, a housing, and a band. The control system monitors and operates the cuff mechanism. The control system monitors the heart sensor. The power system provides electrical power to the control system, the cuff mechanism, and the heart sensor. The control system, the cuff mechanism, the heart sensor, and the power system are located in the housing. The band attaches the wrist to the housing. The medication alert watch: 1) maintains and monitors a plurality of appointments and generates notifications regarding the appointment; 2) monitors the medical status of the person; and, 3) generates notifications regarding the medical status of the person.

8 Claims, 4 Drawing Sheets

MEDICATION ALERT WATCH

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of instruments for display of information, more specifically, an indicating arrangement based on variable medical and veterinary information including information generated through a combination of individual elements.

SUMMARY OF INVENTION

The medication alert watch is a medical instrument that is adapted for use with a person. The medication alert watch is adapted to be worn on a wrist of the person. The medication alert watch comprises a control system, a cuff mechanism, a heart sensor, a power system, a housing, and a band. The control system monitors and operates the cuff mechanism. The control system monitors the heart sensor. The power system provides electrical power to the control system, the cuff mechanism, and the heart sensor. The control system, the cuff mechanism, the heart sensor, and the power system are located in the housing. The band attaches the wrist to the housing. The medication alert watch: 1) maintains and monitors a plurality of appointments and generates notifications regarding the appointment; 2) monitors the medical status of the person; and, 3) generates notifications regarding the medical status of the person.

These together with additional objects, features and advantages of the medication alert watch will be readily apparent to those of ordinary skill in the art upon reading the following detailed description of the presently preferred, but nonetheless illustrative, embodiments when taken in conjunction with the accompanying drawings.

In this respect, before explaining the current embodiments of the medication alert watch in detail, it is to be understood that the medication alert watch is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the medication alert watch.

It is therefore important that the claims be regarded as including such equivalent construction insofar as they do not depart from the spirit and scope of the medication alert watch. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
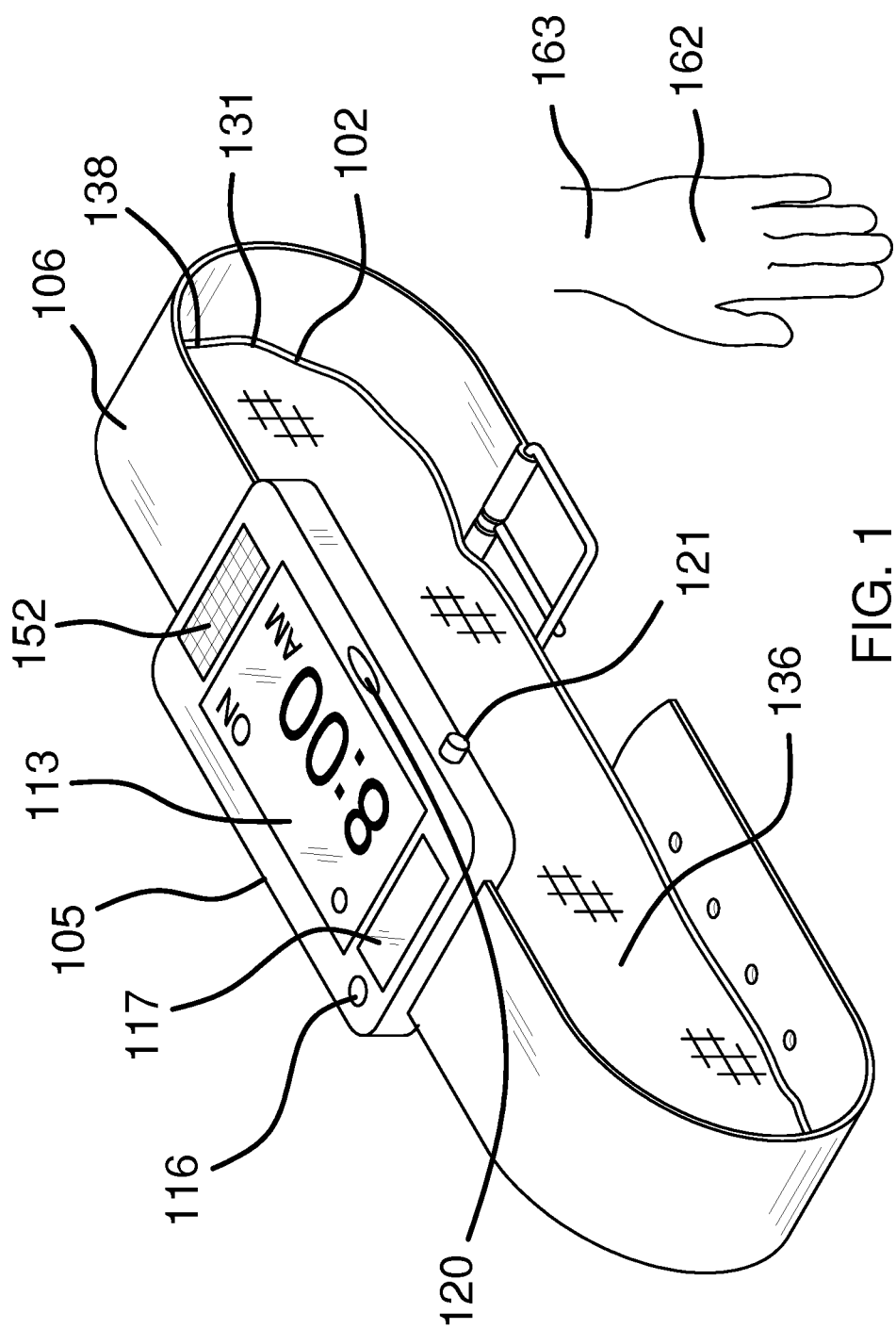
FIG. 1 is a perspective view of an embodiment of the disclosure.
Figure 2:
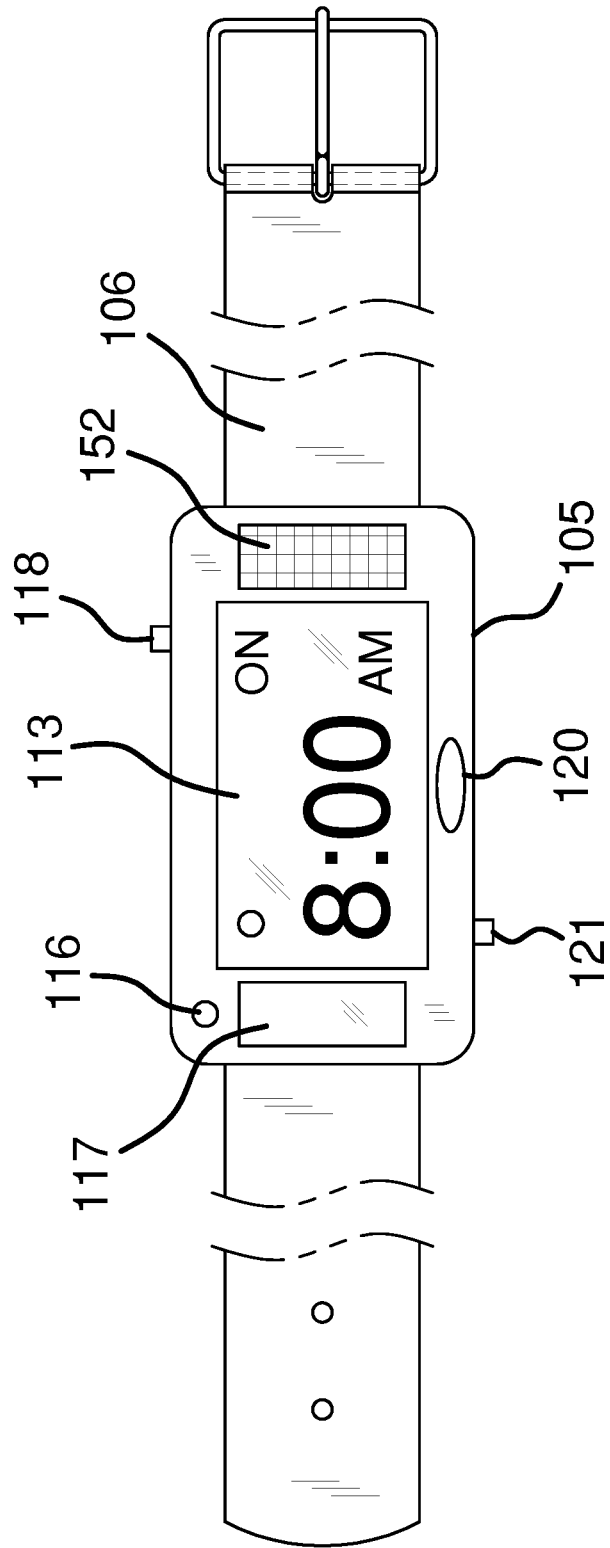
FIG. 2 is a top view of an embodiment of the disclosure.
Figure 3:
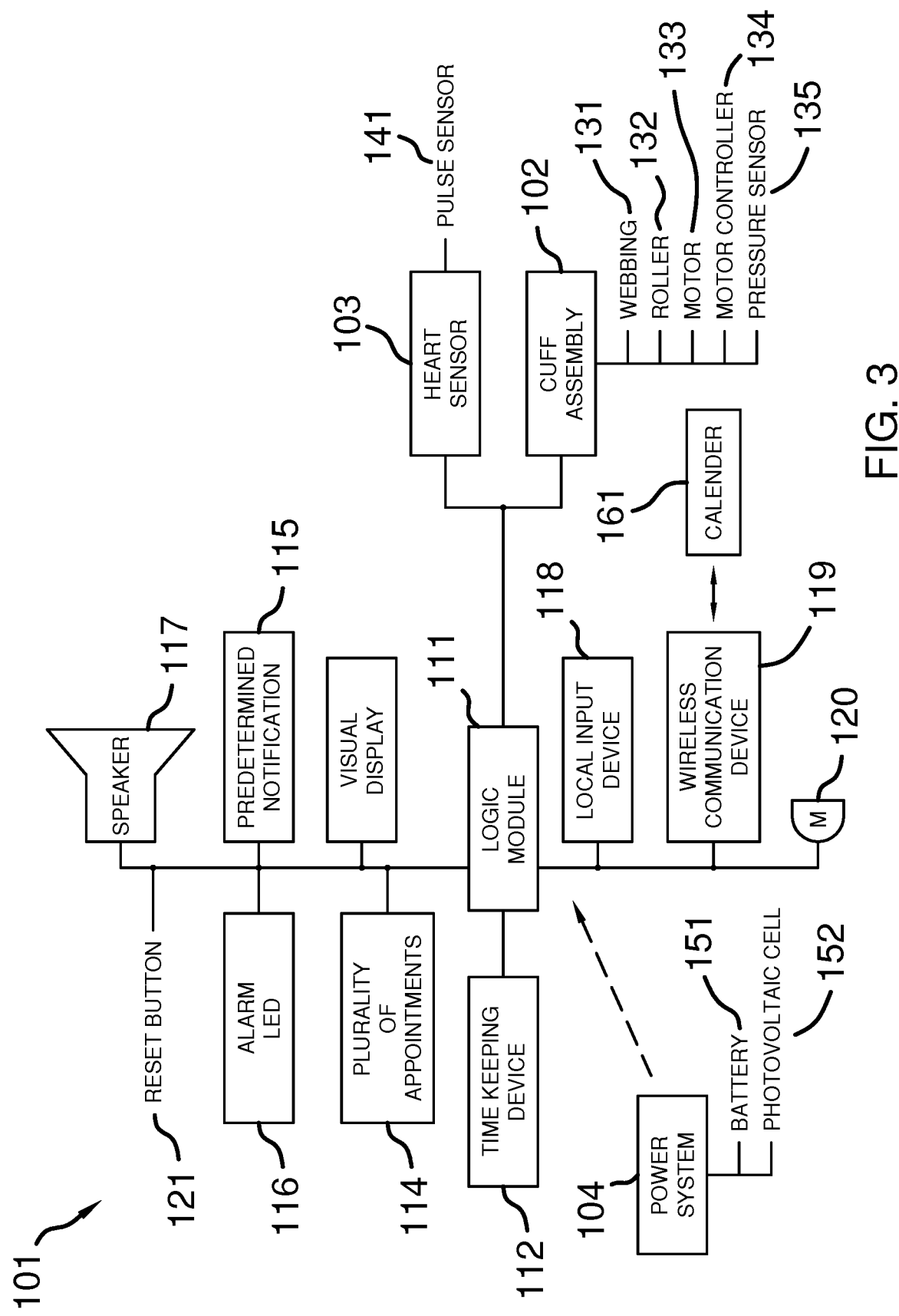
FIG. 3 is a block diagram or schematic view of an embodiment of the disclosure.
Figure 4:
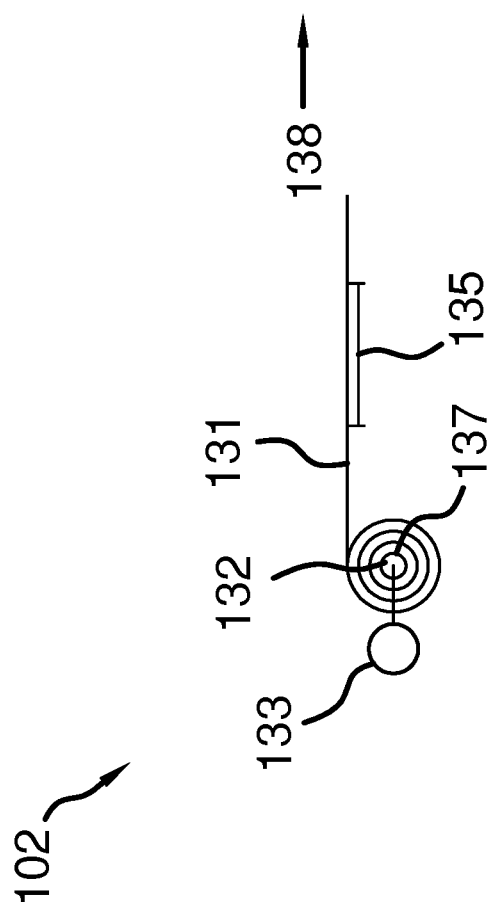
FIG. 4 is a detail view of an embodiment of the disclosure.

Detailed reference will now be made to one or more potential embodiments of the disclosure, which are illustrated in FIGS. 1 through 4.

The medication alert watch 100 (hereinafter invention) comprises a control system 101, a cuff mechanism 102, a heart sensor 103, a power system 104, a housing 105, and a band 106. The control system 101 monitors and operates the cuff mechanism 102. The control system 101 monitors the heart sensor 103. The power system 104 provides electrical power to the control system 101, the cuff mechanism 102, and the heart sensor 103. The control system 101, the cuff mechanism 102, the heart sensor 103, and the power system 104 are located in the housing 105. The band 106 attaches the wrist 163 to the housing 105. The invention 100 is a medical instrument that is adapted for use with a person 162. The invention 100 is adapted to be worn on a wrist 163 of the person 162. The invention 100: 1) maintains and monitors a plurality of appointments 114 and generates notifications regarding each appointment selected from the plurality of appointments 114; 2) monitors the medical status of the person 162; and, 3) generates notifications regarding the medical status of the person 162.

The heart sensor 103 is a sensor that is positioned in contact with the pulse point of the wrist 163 in such a manner as to measure the heart rate. The heart rate is measured in beats per minutes. The heart sensor 103 comprises a pulse sensor 141. The pulse sensor 141 is a commercially available pulse sensor 141. The pulse sensor 141 is an optical device that uses light to measure the motion of the pulse point caused by the beating of the heart. This motion is processed using well known and documented signal processing techniques by the control system 101. The control system 101 receives the signals generated by the pulse sensor 141 and processes these signals to estimate the heart rate. The control system 101 maintains a calculation of the average heart rate over the prior 5 minutes.

The cuff mechanism 102 is a device that monitors blood pressure. The cuff mechanism 102 further monitors the size of the wrist 163. The cuff mechanism 102 comprises a webbing 131, a roller 132, a motor 133, a motor controller 134, and a pressure sensor 135. As shown most clearly in FIG. 1, the webbing 131 is a textile webbing that is attached to the housing 105 to form a loop 136. When the invention 100 is worn, the wrist 163 is inserted through the loop 136. The webbing 131 further comprises a first end 137 and a second end 138. The first end 137 of the webbing 131 is attached to the roller 132 such that the webbing 131 can be rolled on the roller 132. The second end 138 is attached to the housing 105 in a fixed fashion. The roller 132 is a cylindrical device upon which excess lengths of webbing 131 are stored. As shown on FIG. 6, the roller 132 is rotated by the motor 133. The operation of the motor 133 is controlled by a motor controller 134. The motor controller 134 is a device that: 1) turns the motor 133 on and off; 2) manages the direction of rotation of the motor 133; and 3) locks the motor 133 in position such that the webbing 131 cannot be rolled onto or off of the roller 132. As shown most clearly in FIG. 5, a pressure sensor 135 is mounted on the surface of the webbing 131 such that the pressure sensor 135 is in contact with the wrist 163. The pressure sensor 135 is a commercially available piezoelectric sensor that is used to measure the pressure applied to the wrist 163 by the webbing 131.

To measure the blood pressure, the cuff mechanism 102 rotates the motor 133 and the motor controller 134 takes up the webbing 131 onto the roller 132 until the pulse sensor 141 no longer detects a pulse. The motor 133 and the motor controller 134 then slowly let off the webbing 131 from the roller 132. The control system 101 will measure the blood pressure as the pressure measured by the pressure sensor 135 when the heart sensor 103 reacquires a pulse signal from the pulse sensor 141. The cuff mechanism 102 then releases the webbing 131 until the pressure sensor 135 just reaches the zero pressure point. At the zero pressure point, the motor controller 134 locks the roller 132 and the webbing 131 into position. From this position, the control system 101 will continuously monitor the pressure sensor 135. In this configuration, the pressure sensor 135 can be used to measure fluid retention as a sign of cardiac failure. Specifically, fluid retention in these situation will cause the size of the wrist 163 to expand. This size expansion will press the wrist 163 against the webbing 131 and pressure sensor 135 thereby increasing the pressure measured by the pressure sensor 135. The power system 104 provides the electrical energy required to operate the control system 101, the cuff mechanism 102, and the heart sensor 103. The power system 104 comprises a battery 151 and one or more photovoltaic cells 152. The battery 151 is a commercially available battery 151. The chemical energy stored within the battery 151 is renewed and restored through use of the one or more photovoltaic cells 152. The one or more photovoltaic cells 152 are attached to the battery 151 in an electrical circuit that reverses the polarity of the battery 151 and provides the energy necessary to reverse the chemical processes that the battery 151 initially used to generate the electrical energy. This reversal of the chemical process creates a chemical potential energy that will later be used to generate electricity.

The housing 105 is a rigid container that is used to contain the control system 101, the cuff mechanism 102, the heart sensor 103, and the power system 104. The housing 105 is designed such that the visual display 113, the alarm light 116, the speaker 117, the microphone 120, the reset button 121, the webbing 131, the pressure sensor 135, the pulse sensor 141, and the one or more photovoltaic cells 152 are visible and accessible from the exterior of the housing 105. The band 106 is a commercially available strap that is attached to the housing 105 such that the band 106 attaches the housing 105 to the wrist 163.

The control system 101 comprises a logic module 111, a timekeeping device 112, a visual display 113, a plurality of appointments 114, a plurality of notifications 115, an alarm light 116, a speaker 117, a local input device 118, a communication module 119, a microphone 120, and a reset button 121.

The logic module 111 is a commercially available programmable electronic device that is used to manage, regulate, and operate the control system 101. Depending on the specific design and the selected components, the logic module 111 can be a separate component within the in control system 101 or the functions of the logic module 111 can be incorporated into another component within the control system 101. The communication module 119 is a commercially available wireless electronic communication device that allows the logic module 111 to connect with available wireless networks for the purpose of connecting and downloading data from the internet. The timekeeping device 112 is a functionality contained within the control system 101 for the purpose of tracking the date and time within the control system 101. The timekeeping device 112 can be a separate component within the control system 101 or it can be incorporated into the logic module 111. The visual display 113 is an output interface that is used by the logic module 111 to display the time, date, and text-based notifications for use by the person 162. In the first potential embodiment of the disclosure, it is preferred that the display be an LCD display with touchscreen input capabilities.

The plurality of notifications 115 are a collection of audio files that are used by the logic module 111, functioning as an audio source, to generate an audible message over the speaker 117. In the first potential embodiment of the disclosure, it is preferred that the audible messages be spoken messages. The speaker 117 is a transducer, including any necessary associated amplifiers, which takes electrical signals generated by the logic module 111 and converts them into audible acoustic energy. The microphone 120 is a transducer that takes acoustic energy and converts the acoustic energy into electrical energy that is recorded and stored by the logic module 111 to the plurality of notifications 115. It is anticipated that these recorded notifications are one potential source of spoken messages.

The alarm light 116 is a light that is illuminated by the logic module 111 for the purpose of providing a visual indication that a notification has been generated. In the first potential embodiment of the disclosure, it is preferred that the alarm light 116 be an LED. The local input device 118 is a direct connection to the control system 101 for the purpose of entering medication schedules, appointments and other information directly into the control system 101. The use of an LCD display with touchscreen input capabilities to provide the local input device 118 functionality is preferred. However, it is anticipated that future potential embodiments of the disclosure would benefit from the use of switches as the local input device 118. The reset button 121 is a switch.

The reset button 121 is actuated: 1) when the invention 100 is first put on the wrist 163; or, 2) whenever a blood pressure measurement is desired.

A first function of the invention 100 is to track a medication schedule and to monitor the medical status of a person 162 before the medication is taken. Monitoring medical status ensures that medications are not taken in an inappropriate manner. For example, the invention 100 can notify the person 162 that their blood pressure is too low to safely take blood pressure medications. In the first potential embodiment of the disclosure, the medication schedule monitored by the invention 100 is manually loaded using the local input device 118. In a second potential embodiment of the disclosure, the logic module 111 is linked using the communication module 119 to a publically available networked calendaring application. In this scenario, medication schedule is loaded into the publically available networked calendaring application 161 and is subsequently downloaded into the invention 100. Additionally, medical appointments can be loaded into the publically available networked calendaring application 161 to remind the person 162 of upcoming medical appointments. It is anticipated that in the second potential embodiment of the disclosure, the medical professionals caring for the person 162 will directly enter the medication schedules and medical appointments as the plurality of appointments 114 into the publically available networked calendaring application 161 which will be downloaded into the control system 101 and managed by the logic module 111.

A second function of the invention 100 is to monitor the medical status of the person 162. In the first potential embodiment of the disclosure, the pulse sensor 141 and the pressure sensor 135 are monitored continuously. The blood pressure is taken: 1) when the reset button 121 is pushed; or, 2) one minute before notification to take a medication is given. In the first potential embodiment of the disclosure, the following events will cause the logic module 111 to generate notifications: 1) the measured heart rate falls below a predetermined default rate (default 60 beats per minute); 2) the measured heart rate falls 15% below the average heart rate of the prior five minutes; 3) the systolic blood pressure has fallen below a predetermined level (default 110 mmHg); or 4) an increase in pressure as measured by the pressure sensor 135 is detected.

The following definitions were used in this disclosure:

Audio File: As used in this disclosure, an audio file is a digital representation of a sound that is used to store a recording of the sound. Separate hardware is used to convert the digital representation of the sound into an audible sound.

Audio Source: As used in this disclosure, an audio source is a device that generates electrical signals that can be converted in to audible sounds by a speaker.

Band: As used in this disclosure, a band is a flat loop of material.

Battery: As used in this disclosure, a battery is a container consisting of one or more cells, in which chemical energy is converted into electricity and used as a source of power.

Control System: As used in this disclosure, a control system is a first device or system that manages and regulates the behavior or operation of a second device or system.

Diode: As used in this disclosure, a diode is a two terminal semiconductor device that allows current flow in only one direction.

Display: As used in this disclosure, a display is a surface upon which is projected an image, potentially including, but not limited to, graphic images and text, that is interpretable by an individual viewing the projected image in a meaningful manner.

Electric Motor: In this disclosure, an electric motor is a machine that converts electric energy into rotational mechanical energy.

Exterior: As used in this disclosure, the exterior is use as a relational term that implies that an object is not contained within the boundary of a structure or a space.

Housing: As used in this disclosure, a housing is a rigid casing that encloses and protects one or more devices.

Interior: As used in this disclosure, the interior is use as a relational term that implies that an object is contained within the boundary of a structure or a space.

LCD: As used in this disclosure, LCD is an acronym for Liquid Crystal Display. A liquid crystal display comprises a liquid crystal film placed between two sheets of transparent material. The visual characteristics of the can be varied through the application of a voltage.

LED: As used in this disclosure, an LED is an acronym for a light emitting diode. A light emitting diode is a diode that is also a light source. Because of close operational correspondence of the function of the cathode and anode of an organic LEDs and the cathode and anode of a semiconductor LED, organic LEDs are included in this definition.

Light: As used in this disclosure, a light is an electrical device that generates visible light to illuminate objects so they can be seen.

Logic Module: As used in this disclosure, a logic module is an electrical device that is programmable and that accepts digital and analog inputs, processes the digital and analog inputs according to previously stored instruction and provides the results of these instructions as digital or analog outputs.

Loop: As used in this disclosure, a loop is the length of a first linear structure including, but not limited to, lines, cords, or ribbons, that is: 1) folded over and joined at the ends forming an enclosed space; or, 2) curved to form a closed or nearly closed space within the first linear structure. In both cases, the space formed within the first linear structure is such that a second linear structure such as a line, cord or a hook can be inserted through the space formed within the first linear structure. Within this disclosure, the first linear structure is said to be looped around the second linear structure.

Microphone: As used in this disclosure, a microphone is a transducer that converts the energy from vibration into electrical energy. The sources of vibrations include, but are not limited to, acoustic energy.

Motor: As used in this disclosure, a motor refers to the method of transferring energy from an external power source into mechanical energy.

Photovoltaic Cell: As used in this disclosure, a photovoltaic cell is an electrical device that directly converts light energy into electrical energy.

Roller: As used in this disclosure, a roller is a cylindrical device a flexible strip or cord like object is wrapped, or "rolled" for storage.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Speaker: As used in this disclosure, a speaker is an electrical device that converts an electrical signal into an audible sound.

Strap: As used in this disclosure a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Textile: As used in this disclosure, a textile is a material that is woven, knitted, braided or felted. Synonyms in common usage for this definition include fabric and cloth.

Transducer: As used in this disclosure, a transducer is a device that converts a physical quantity, such as pressure or brightness into an electrical signal or a device that converts an electrical signal into a physical quantity.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. An indicating arrangement comprising:
   a computer, a cuff mechanism, a heart sensor, a power system, a housing, and a band;
   wherein the computer monitors and operates the cuff mechanism;
   wherein the computer monitors the heart sensor;
   wherein the power system provides electrical power to the control system, the cuff mechanism, and the heart sensor;
   wherein the computer, the cuff mechanism, the heart sensor, and the power system are located in the housing;
   wherein the indicating arrangement is a medical instrument that is adapted for use with a person;
   wherein the indicating arrangement is adapted to be worn on a wrist of the person;
   wherein the band attaches the wrist to the housing;
   wherein the indicating arrangement maintains and monitors a plurality of appointments;
   wherein the indicating arrangement generates notifications regarding each appointment selected from the plurality of appointments;
   wherein the indicating arrangement monitors the medical status of the person;
   wherein the indicating arrangement generates notifications regarding the medical status of the person;
   wherein the heart sensor is a sensor that is adapted to be positioned in contact with the pulse point of the wrist;
   wherein the heart sensor comprises a pulse sensor;
   wherein the computer receives the signals generated by the pulse sensor and processes these signals to estimate the heart rate;
   wherein the computer maintains a calculation of the average heart rate over the prior five minutes;
   wherein the cuff mechanism is a device that monitors blood pressure;
   wherein the cuff mechanism further monitors the size of the wrist;
   wherein the cuff mechanism comprises a webbing, a roller, a motor, a motor controller, and a pressure sensor;
   wherein the webbing is stored on the roller;
   wherein the motor and motor controller rotate the roller;
   wherein the operation of the motor is controlled by a motor controller;
   wherein the pressure sensor attaches to the webbing;
   wherein the webbing is a textile;
   wherein the webbing forms a loop;
   wherein the loop is adapted to receive the wrist;
   wherein the webbing further comprises a first end and a second end;
   wherein the first end of the webbing is attached to the roller;
   wherein the second end is attached to the housing in a fixed fashion;
   wherein the roller is a cylindrical device;
   wherein the motor controller turns the motor on and off;
   wherein the motor controller manages the direction of rotation of the motor;
   wherein the motor controller locks the motor in position such that the webbing cannot be rolled onto or off of the roller;
   wherein the pressure sensor is mounted on the surface of the webbing such that the pressure sensor is in contact with the wrist;
   wherein the pressure sensor is a piezoelectric sensor;
   wherein the pressure sensor measures the pressure applied to the wrist by the webbing;
   wherein the power system provides the electrical energy required to operate the computer, the cuff mechanism, and the heart sensor;
   wherein the power system comprises a battery and one or more photovoltaic cells;
   wherein the chemical energy stored within the battery is renewed and restored through use of the one or more photovoltaic cells;
   wherein the one or more photovoltaic cells are attached to the battery such that the battery provides the energy necessary to reverse the chemical processes that the battery initially used to generate the electrical energy;
   wherein the housing is a rigid container;
   wherein the housing contains the control system, the cuff mechanism, the heart sensor, and the power system;
   wherein the band attaches the housing to the wrist;
   wherein the computer comprises a logic module, a timekeeping device, a visual display, a plurality of appointments, a plurality of notifications, an alarm light, a speaker, a local input device, a microphone, and a reset button;

wherein the logic module is an electronic device that manages, regulates, and operates the control system;

wherein the timekeeping device tracks the date and time;

wherein the visual display is an output interface;

wherein the plurality of notifications are a collection of audio files that are used by the logic module to generate an audible message over the speaker;

wherein the alarm light is a light that is illuminated by the logic module;

wherein the local input device is directly connected to the control system;

wherein the reset button is an electric switch;

wherein the computer further comprises a communication module;

wherein the communication module is a commercially available wireless electronic communication device that allows the logic module to connect with available wireless networks for the purpose of connecting and downloading data from the internet;

wherein a first function of the indicating arrangement is to track a medication schedule and to monitor the medical status of a person before the medication is taken.

2. The indicating arrangement according to claim 1 wherein the pulse sensor is an optical device.

3. The indicating arrangement according to claim 2 wherein the visual display is an LCD display with touch-screen input capabilities.

4. The indicating arrangement according to claim 3 wherein the alarm light is an LED;

wherein the visual display, the alarm light, the speaker, the microphone, the reset button, the webbing, the pressure sensor, the pulse sensor, and the one or more photovoltaic cells are visible and accessible from the exterior of the housing.

5. The indicating arrangement according to claim 1 wherein the pulse sensor and the pressure sensor are monitored continuously;

wherein the blood pressure is taken when the reset button is pushed;

wherein the blood pressure is taken one minute before a notification selected from the plurality of notifications is generated;

wherein a notification selected from the plurality of notifications is generated when the measured heart rate falls below a predetermined default rate;

wherein a notification selected from the plurality of notifications is generated when the measured heart rate falls below the average heart rate over the prior five minutes;

wherein a notification selected from the plurality of notifications is generated when the systolic blood pressure has fallen below a predetermined level;

wherein a notification selected from the plurality of notifications is generated when an increase in pressure as measured by the pressure sensor is detected.

6. The indicating arrangement according to claim 5 wherein the pulse sensor is an optical device.

7. The indicating arrangement according to claim 6 wherein the visual display is an LCD display with touch-screen input capabilities.

8. The indicating arrangement according to claim 7 wherein the alarm light is an LED;

wherein the visual display, the alarm light, the speaker, the microphone, the reset button, the webbing, the pressure sensor, the pulse sensor, and the one or more photovoltaic cells are visible and accessible from the exterior of the housing.

* * * * *